US00PP16459P2

(12) United States Plant Patent
Sakazaki

(10) Patent No.: US PP16,459 P2
(45) Date of Patent: Apr. 18, 2006

(54) *ANAGALLIS* PLANT NAMED 'USANG-4'

(50) Latin Name: *Anagallis hybrida*
Varietal Denomination: USANG-4

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 78 days.

(21) Appl. No.: 10/955,490

(22) Filed: Sep. 30, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP15,136 P2 * 9/2004 Freyre ..... Plt./263
PP15,137 P2 * 9/2004 Freyre ..... Plt./263

OTHER PUBLICATIONS

UPOV ROM GTITM Computer Database, GTI Jouve Retrieval Software 2005/02 Citation for 'USANG4'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Anagallis* plant named 'USANG-4', characterized by its compact, low-trailing and outwardly spreading plant habit; moderately vigorous growth habit; freely branching habit; numerous fragrant single flowers that are pink in color with red purple centers; and good garden performance.

1 Drawing Sheet

Botanical classification: *Anagallis hybrida.*
Cultivar denomination: 'USANG-4'.

BACKGROUND OF THE INVENTION

The present Invention relates to a new and distinct cultivar of *Anagallis* plant, botanically known as *Anagallis hybrida,* and hereinafter referred to by the cultivar name USANG-4.

The new *Anagallis* is a product of a planned breeding program conducted by the Inventor in Hikone Shiga, Japan. The objective of the breeding program is to create new compact *Anagallis* plants with freely flowering habit and attractive flower coloration.

The new *Anagallis* originated from a cross-pollination made by the Inventor on May 25, 1999 of an unnamed selection of *Anagallis filiformis,* not patented, as the female, or seed parent, with an unnamed selection of *Anagallis hybrida*, not patented, as the male, or pollen parent. The new *Anagallis* was discovered and selected as a single plant from within the resulting progeny of the cross-pollination in Bonsall, Calif. on May 12, 2000.

Asexual reproduction of the new cultivar by terminal vegetative cuttings since Jul. 1, 2000 in Bonsall, Calif. has shown that the unique features of this new *Anagallis* are stable and reproduced true to type in successive generations.

SUMMARY OF THE INVENTION

Plants of the cultivar USANG-4 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'USANG-4'. These characteristics in combination distinguish 'USANG-4' as a new and distinct cultivar:

1. Compact, low-trailing and outwardly spreading plant habit.
2. Moderately vigorous growth habit.
3. Freely branching habit.
4. Numerous fragrant single flowers that are pink in color with red purple centers.
5. Good garden performance.

In side-by-side comparisons conducted in Bonsall, Calif., plants of the new *Anagallis* differed from plants of the female parent selection, in the following characteristics:

1. Plants of the new *Anagallis* were more vigorous than plants of the female parent selection.
2. Plants of the new *Anagallis* had larger flowers than plants of the female parent selection.

In side-by-side comparisions conducted in Bonsall, Calif., plants of the new *Anagallis* differed from plants of the male parent selection, in the following characteristics:

1. Plants of the new *Anagallis* were more vigorous than plants of the male parent selection.
2. Plants of the new *Anagallis* had larger flowers than plants of the male parent selection.

Plants of the new *Anagallis* can be compared to plants of the *Anagallis* cultivar Wildcat Orange, disclosed in U.S. Plant Pat. No. 15,136. In side-by-side comparisons conducted in Bonsall, Calif., plants of the new *Anagallis* differed from plants of the cultivar Wildcat Orange in the following characteristics:

1. Plants of the new *Anagallis* were more trailing than and not as upright as plants of the cultivar Wildcat Orange.
2. Plants of the new *Anagallis* had pink-colored flowers whereas plants of the cultivar Wildcat Orange had orange-colored flowers.
3. Flowers of plants of the new *Anagallis* were fragrant whereas flowers of plants of the cultivar Wildcat Orange were not fragrant.

BRIEF DESCRIPTION OF THE PHOTOGRAPHS

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Anagallis*.

The photograph at the top of the sheet is a close-up view of typical flowers and leaves of 'USANG-4'.

The photograph at the bottom of the sheet comprises a side perspective viewof a typical plant of 'USANG-4' grown in a container.

DETAILED BOTANICAL DESCRIPTION

The aforementioned photographs and following observations and measurements describe plants grown in Bonsall, Calif., in a polyethylene-covered greenhouse during the late spring under full sun conditions with day temperatures ranging from about 16° C. to about 38° C. and night temperatures ranging from about 13° C. to about 18° C. After planting rooted cuttings, plants were grown for about seven weeks in 12.5 cm containers. Color refernces are made to The Royal Horticultural Society Colour Chart, 1995 Edition, except where general terms of ordinary dictionary significance are used.

Botanical classification: *Anagallis hybrida* cultivar USANG-4.

Parentage:

*Female parent.*—Unnamed selection of *Anagallis filiformis,* not patented.

*Male parent.*—Unnamed selection of *Anagallis hybrida*, not patented.

Propagation:

*Type cutting.*—Terminal vegetative cuttings.

*Time to initiate roots, summer.*—About five days at 24° C.

*Time to initiate roots, winter* .—About seven days at 24° C.

*Time to develop roots, summer.*—About 20 days at 24° C.

*Time to develop roots, winter.*—About 25 days at 24° C.

*Root description.*—Fine, fibrous; white, close to 155 D, in color.

*Rooting habit.*—Freely branching.

Plant description:

*Form/growth habit.*—Annual flowering plant; compact; initially upright, then low-trailing and outwardly spreading; uniformly mounded plant form. Freely branching habit with about 75 lateral branches. Moderately vigorous.

*Plant height.*—About 5 cm.

*Plant diameter.*—(*area of spread*), *single plant.*—About 32 cm.

*Lateral branches.*—Length: About 18 cm. Diameter: About 2 mm. Internode length: About 1.5 cm. Texture: Smooth, glabrous. Color: 182A.

*Foliage description.*—Arrangement: Opposite; simple. Length: About 1.2 cm. Width: About 1.1 cm. Shape: Oval to ovate. Apex: Rounded to broadly acute. Base: Attenuate. Margin: Entire. Texture, upper and lower surfaces: Glabrous, smooth. Venation pattern: Pinnate, arcuate. Color: Developing leaves, upper and lower surfaces: 146B. Fully expanded leaves, upper and lower surfaces: 147A. Venation, upper surface: 147A. Venation, lower surface: 146B. Petiole: Length: About 3 mm. Diameter: About 1 mm. Texture, upper and lower surfaces: Smooth, glabrous. Color, upper and lower surfaces: 144A.

Flower description:

*Flower type and habit.*—Single star-shaped flowers; flowers face mostly upward or outward; terminal or axillary; freely flowering habit, about 24 flowers and/or buds per lateral branch at one time.

*Natural flowering season.*—Plants flower from June through September in Bonsall, Calif., flowering continuous during this period. Plants start flowering about five weeks after planting rooted cuttings. Flowers persistent.

*Flower longevity on the plant.*—About four to five days.

*Fragrance.*—Cinnamon-like.

*Flower size.*—Diameter: About 1.6 cm. Depth (height): About 1.1 cm.

*Flower buds.*—Length: About 9 mm. Diameter: About 3 mm. Shape: Ovoid. Color: 62A.

*Petals.*—Quantity/arrangement: About five petals arranged in a single whorl. Length: About 1.1 cm. Width: About 4 mm. Shape: Obovate. Apex: Rounded. Base: Attenuate. Margin: Entire. Texture, upper and lower surfaces: Smooth, satiny. Color: When opening, upper surface: 62A. When opening, lower surface: 62B. Fully opened, upper surface: 62A; towards base, 63A ; color becoming close to 62C to 62D with development. Fully opened, lower surface: 62 A.

*Sepals.*—Arrangement/appearance: Five sepals arranged in a single whorl; star-shaped. Length: About 6 mm. Width: About 1 mm. Shape: Linear. Apex: Acuminate. Base: Fused. Margin: Entire. Texture, upper and lower surfaces: Smooth, glabrous. Color, upper and lower surfaces: 146A.

*Peduncles.*—Length: About 2.7 cm. Width: About 1 mm. Angle: About 50° C. to 90° C. from the main stem. Strength: Strong. Texture: Smooth, glabrous. Color: 144A.

*Reproductive organs.*—Stamens: Quantity per flower: About five. Anther shape: Oval. Anther length: Less than 1 mm. Anther color: 10C. Pollen amount: Scarce. Pollen color: 10C. Pistils: Quantity per flower: One. Pistil length: About 8 mm. Style length: About 5 mm. Style color: 62C and 62D. Stigma shape: Rounded. Stigma color: 62B. Ovary color: 144A.

*Seed/fruit.*—Seed and/or fruit production has not been observed.

Disease/pest resistance: Plants of the new *Anagallis* have not been noted to be resistant to pathogens or pests common to *Anagallis*.

Garden performance: Plants of the new *Anagallis* have been observed to have good garden performance. Plants of the new *Anagallis* have been noted to tolerate temperatures from below 0 to 40° C. and have execellent tolerance to rain and wind.

It is claimed:

1. A new and distinct cultivar of *Anagallis* plant named 'USANG-4', as illustrated and described.

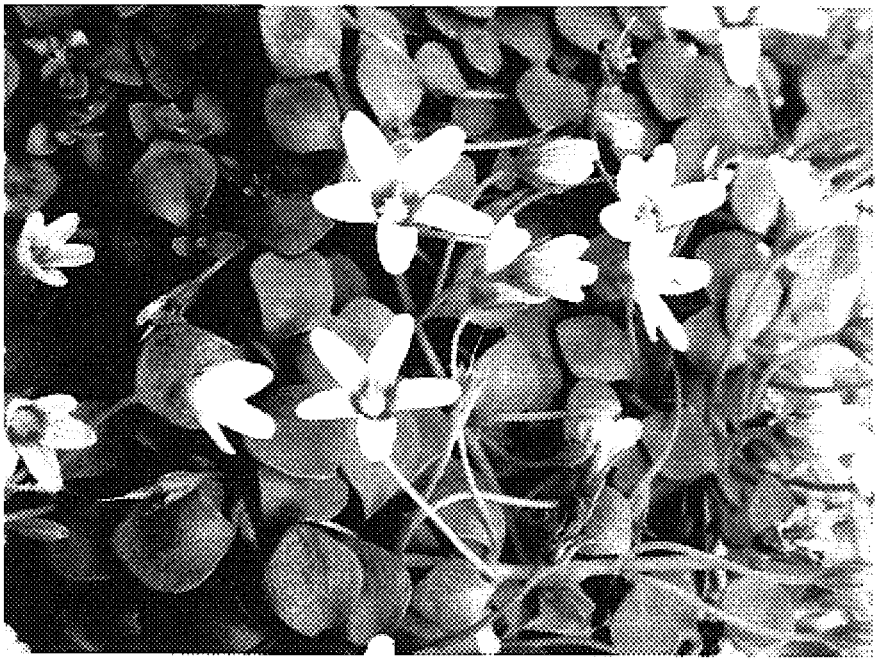
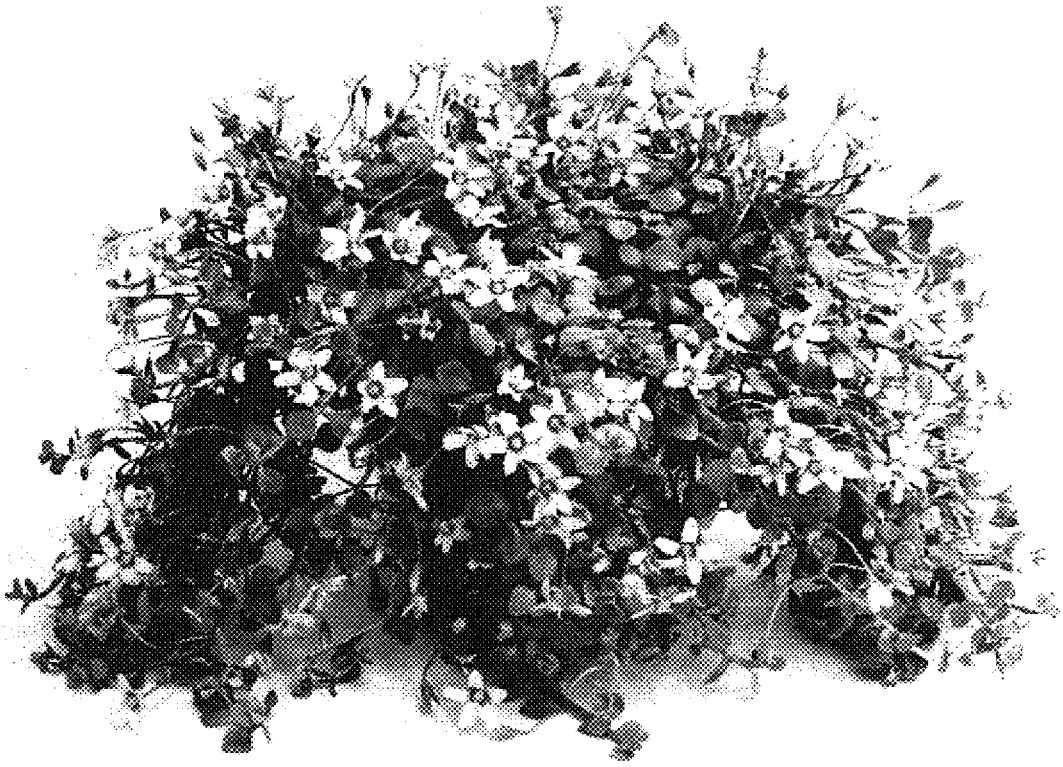

* * * * *